(12) United States Patent
Mäntylä et al.

(10) Patent No.: US 11,841,357 B2
(45) Date of Patent: Dec. 12, 2023

(54) MEASUREMENT APPARATUS AND METHOD OF PAPER WEB

(71) Applicant: VALMET AUTOMATION OY, Espoo (FI)

(72) Inventors: Markku Mäntylä, Kangasala (FI); Pekka Suopajärvi, Oulu (FI)

(73) Assignee: VALMET AUTOMATION OY, Espoo (FI)

( * ) Notice: Subject to any disclaimer, the term of this patent is extended or adjusted under 35 U.S.C. 154(b) by 627 days.

(21) Appl. No.: 17/004,697

(22) Filed: Aug. 27, 2020

(65) Prior Publication Data
US 2021/0088500 A1    Mar. 25, 2021

(30) Foreign Application Priority Data
Sep. 23, 2019  (FI) ........................... 20195795

(51) Int. Cl.
*G01N 21/3559*    (2014.01)
*G01N 33/34*    (2006.01)
(Continued)

(52) U.S. Cl.
CPC ........... *G01N 33/346* (2013.01); *D21F 7/003* (2013.01); *D21F 7/06* (2013.01); *G01N 21/3559* (2013.01);
(Continued)

(58) Field of Classification Search
CPC .. G01N 33/346; G01N 21/3559; G01N 21/86; G01N 2021/8663; D21F 7/003; D21F 7/06

See application file for complete search history.

(56) References Cited

U.S. PATENT DOCUMENTS 3,793,524 A    2/1974  Howarth
8,975,586 B2    3/2015  Krolak et al.
(Continued)

FOREIGN PATENT DOCUMENTS

WO    WO-2019173900 A1 *  9/2019 ............. G01B 11/02

OTHER PUBLICATIONS

Apr. 23, 2020 Office Action issued in Finnish Patent Application No. 20195795.
(Continued)

*Primary Examiner* — Anthony Calandra
*Assistant Examiner* — Stephen M Russell
(74) *Attorney, Agent, or Firm* — Oliff PLC

(57) ABSTRACT

A measurement apparatus of a moving paper web, includes an optical radiation source that outputs optical radiation toward a scattering element of the measurement apparatus. The scattering element scatters the optical radiation, and a transmitting surface of the scattering element directs the optical radiation in a scattered manner toward the moving paper web. A distance between said transmitting surface of the scattering element and a surface of the paper web is known, and the transmitting surface and a detector of the apparatus are on opposite sides of the paper web. The detector receives at least a part of the optical radiation, which is side-scattered from the moving paper web. The detector determines a moisture value and a dry weight of the paper web on the basis of spectral information on the received optical radiation and the known distance.

14 Claims, 4 Drawing Sheets

(51) Int. Cl.
*G01N 21/86* (2006.01)
*D21F 7/00* (2006.01)
*D21F 7/06* (2006.01)

(52) U.S. Cl.
CPC ..... *G01N 21/86* (2013.01); *G01N 2021/8663* (2013.01)

(56) References Cited

U.S. PATENT DOCUMENTS

| | | | | |
|---|---|---|---|---|
| 2015/0136993 A1* | 5/2015 | Mantyla | ................ | G01N 21/31 250/372 |
| 2016/0122946 A1* | 5/2016 | Mäntylä | ............. | B05C 11/1015 118/712 |

OTHER PUBLICATIONS

Oct. 15, 2021 Office Action issued in Finnish Patent Application No. 20195795.

* cited by examiner

MEASUREMENT APPARATUS AND METHOD OF PAPER WEB

FIELD

The invention relates to a measurement apparatus and method of a moving paper web.

BACKGROUND

Attempts have been made to assess certain physical properties of a paper web optically. However, an optical measurement of a combination of several physical properties together from the paper web have failed or proved too unreliable.

Hence, there is a need to develop the measurements.

BRIEF DESCRIPTION

The present invention seeks to provide an improved measurement. The invention is defined by the independent claims. Embodiments are defined in the dependent claims.

LIST OF DRAWINGS

Example embodiments of the present invention are described below, by way of example only, with reference to the accompanying drawings, in which FIG. 1A illustrates an example of a paper web measurement apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1A:
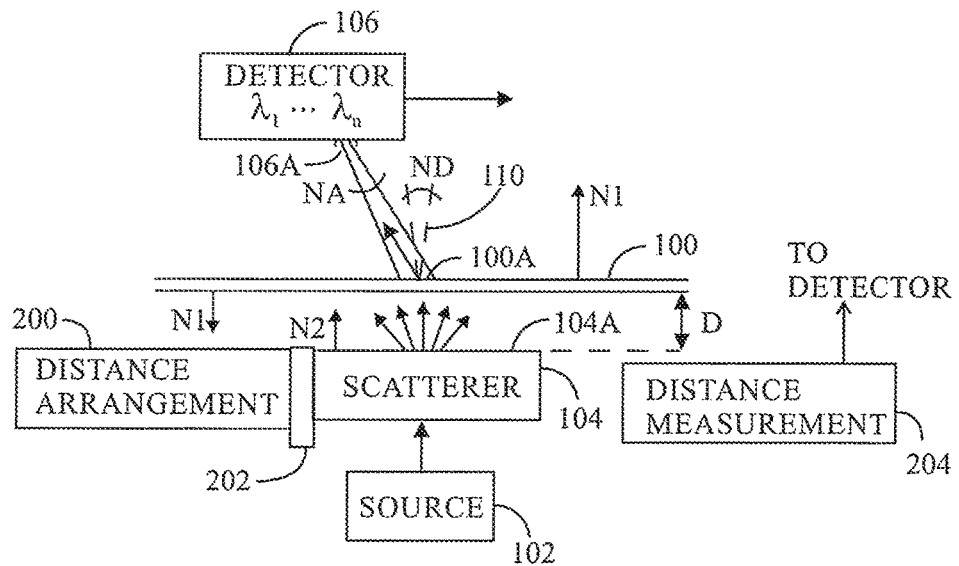
FIG. 1B illustrates another example of the paper web measurement apparatus.
FIG. 1C illustrates an example of a deviation (angle) of accepted rays of optical radiation scattered from the paper web from a normal of the paper web.
FIG. 1D illustrates an example how to gather the scattered optical radiation from a target area of the paper web.

FIG. 1A illustrates an example of a measurement apparatus of a paper web 100. The paper web 100 may also be called paper sheet. The paper web 100, which may be moving during the measurement, may comprise a tissue paper web, for example. The tissue paper web, in turn, is at least partially made of plant fibers, woody plant fibers and/or wood fibers. The apparatus comprises an optical radiation source 102 that outputs optical radiation toward a scattering element 104 of the measurement apparatus. The paper web 100 is not between the optical radiation source 102 and the scattering element 104. The optical radiation source 102 may be any source, which transmits the wavelengths that are measured or detected. The optical radiation source 102 may comprise a wide band source. The optical radiation source 102 may emit in visible and infrared spectrum. The optical radiation source 102 may comprise at least one halogen lamp, at least one led, their combination or the like, for example.

The scattering element 104 scatters the optical radiation, and a transmitting surface 104A of the scattering element 104 directs the optical radiation in a scattered manner toward the moving paper web 100. The average scattering direction of the scattered optical radiation from the transmitting surface 104A may be about parallel to a normal N1 of the paper web 100, although a deviation or variation between the scattering direction and the normal N1 may be allowable. In an embodiment, the scattering element 104 may cause the optical radiation to scatter within the scattering element 104. In an embodiment, the scattering element 104 may cause the optical radiation to scatter at a surface of the scattering element 104. In an embodiment, the scattering element 104 may cause the optical radiation to scatter both at a surface of the scattering element 104 and within the scattering element 104. The surface that causes the scattering of the optical radiation may be the transmitting surface 104A.

A normal N2 of said transmitting surface 104A of the scattering element 104 may be parallel to a normal N1 of the paper web 100, although a deviation or variation between the normal N1 and the normal N2 may be allowable. If there is a non-zero angle between the normal N1 and the normal N2 which keeps constant or its variation is known, the measurement can be calibrated such the effect of the non-zero angle deviation or the variation between the normal N1 and the normal N2 to the measurement can be eliminated or reduced for allowing proper results from the measurement.

However, a distance D between the transmitting surface 104A of the scattering element 104 and a surface of the paper web 100 is, is assumed or is kept known during the measurement. That the distance D is known may mean that the distance D is constant or it varies in a deterministic manner as a function of time. If the distance D varies in the deterministic manner, its potentially disturbing effect to the measurement can be compensated. The effect of the varying distance D may be determined at any moment separately or it may be statistically approximated in a time-window.

By keeping the distance D deterministic, rays of the optical radiation scattered by the scattering element 104 have a known and/or deterministic distribution on the paper web 100, which improves the measurement. By keeping the distance D constant, rays of the optical radiation scattered by the scattering element 104 have a constant distribution on the paper web 100, which also improves the measurement. Said transmitting surface 104A and a detector 106 of the apparatus are on opposite sides of the paper web 100 in a direction parallel to said normals N1 and N2.

The detector 106 receives at least a part of the optical radiation, which is side-scattered from the moving paper web 100. The detector 106 may reject the optical radiation, which has passed directly without scattering through the moving paper web 100. The non-scattered optical radiation 110 propagates mainly in a direction parallel to the normal N1 of the paper web 100. In an embodiment, the detector 106 may have a blocking component (not shown in Figures) that prevents propagation of the optical radiation that has passed without scattering through the moving paper web 100 to a sensor 152 (see FIG. 1D). The blocking component may be made of material non-transparent to the optical radiation used in the measurement. Additionally or alternatively, the detector 106 may receive the side-scattered optical radiation only from directions, which deviate from the direction of the normal N1 of the paper web 100 by at least a predetermined angle (see FIG. 1C).

In an embodiment, an angular deviation ND of a forward scattered optical radiation 110, which also includes the non-scattered optical radiation, from the normal N1 of the paper web 100 can be considered at maximum about the same as an accepted angular deviation NA of the detector 106. The accepted angular deviation NA may be the same as a numerical aperture of the detector 106. The detector 106 may reject the forward scattered optical radiation.

The scattering element 104 may comprise translucent material and/or a plate the transmitting surface 104A of which is optically rough. The scattering element 104 may be made of glass, sapphire, fused silica, gallium nitride and/or polymer, for example. The scattering element 104 may comprise holographs to cause scattering. The scattering may be caused by particles in a medium. The particles may be comprise powder or fibers of a suitable material. The particles may be include polycrystalline material such as marble and/or calcium fluoride. The selection of materials depend on the measured wavelengths in order to have a desired scattering effect.

The scattering element 104 may cause single or multiple scattering. The single scattering randomize rays of the optical radiation to a certain extent and the multiple scattering randomize the rays of the optical radiation more. When the scattering element 104 is based on the multiple scattering, it can be considered that the scattering element 104 diffuses the optical radiation. In that case, the scattering element 104 can also be called a diffuser. The scattering element 106, which diffuses the optical radiation, may be considered a Lambertian diffuser.

The scattering element 104 enables a calibration measurement when the paper web 100 is not between the scattering element 102 and the detector 106. Then the detector 106 receives the scattered optical radiation directly from the scattering element 104. The intensity of the scattered optical radiation from the paper web 100 may be compared with the intensity of the scattered optical radiation scattered directly from the scattering element 104. The effect of dry matter and water of the paper web 100 can be detected in the comparison because the dry matter and the water in the paper web 100 cause variation in the intensity at the measured wavelength bands.

The scattering element 104 alleviates a requirement for a dynamical range of the detector 106, when compared with the prior art measurement where the optical power source 102 illuminates directly the detector 106 during a calibration measurement. Namely, when the paper web 100 is not between the optical power source 102 and the detector 106 and the optical power source 102 illuminates the detector 106 directly, the received optical power at the detector 106 is rather high. Then, when the paper web 100 is between the optical power source 102 and the detector 106 and the optical power source 102 illuminates the paper web 100, which scatters the optical radiation to the detector 106, the received optical power at the detector 106 is rather low.

The detector 106 has a receiving aperture 106A, which receives the optical radiation from the paper web 100, above the paper web 100, and receiving aperture 106A does not overlap with a target area 100A, from which the receiving aperture 106A receives the optical radiation. That is, the receiving aperture 106A is not within a closed border line made of the normals N1 located at an outer contour of the target area 100A, which the receiving aperture 106A receives the optical radiation from. In other words, the receiving aperture 106A and the target area 100A do not directly face each other in the direction of the normal N1 of the paper web 100.

The detector 106 is configured determine a moisture value MOI and a dry weight OD (Oven Dry) of the paper web 100 on the basis of spectral information carried by the received optical radiation. The moisture value MOI may be a moisture percentage MOI % or a water weight WW. The measurement of the moisture value MOI and the dry weight OD (Oven Dry) may be made repeatedly. The repetition rate of the measurement may be in a range 1 Hz to 100000 Hz, for example. A final measurement or output results of the moisture value MOI and the dry weight OD (Oven Dry) may be based on averaging a plurality of measurements.

A basis weight BW is a sum of the dry weight OD and the water weight WW, which may be expressed in a mathematical form as BW=OD+WW. The water weight WW, in turn, can be formed as a multiplication between the dry weight OD and the moisture percentage MOI % divided by dry percentage DRY %, which may be expressed in a mathematical form as WW=(MOI %*OD)/(100%−MOI %). More generally, the moisture percentage may be expressed as a relative amount of water. Then the percentage signs may be omitted and the mathematical form becomes WW= (MOI*OD)/(1−MOI), where MOI is the relative amount of water corresponding to and being actually the same as the moisture percentage MOI %.

In an embodiment, the detector 106 may receive the side-scattered optical radiation only from directions, which deviate from the direction of the normal N1 of the paper web 100 by at least a predetermined angle. That is, the detector 106 receives rays of the side-scattered optical radiation only from directions, whose directions deviate from the direction of the normal N1 of the paper web 100 by at least the predetermined angle φ (see FIG. 1C). The predetermined angle φ may be constant or time-dependent φ(t), where t is time. The predetermined angle may be known at any moment or it may be statistically approximated in a time-window. The predetermined angle φ is an angle between the normal N1 of the paper web 100 and a middle ray of the side-scattered optical radiation propagating to detection through the receiving aperture 106A. In other words, the middle ray may be a center of an intensity distribution of the side-scattered optical radiation received by the receiving aperture 106A. A value of the predetermined angle φ may in a range 8° to 82°, for example. The maximum deviation from the normal N1 for the directions of the rays of the side-scattered optical radiation is naturally 90°. Thus, the rays of the side-scattered optical radiation may be detected only if they are in the angular range from the predetermined angle to 90°.

In an embodiment, the predetermined angle φ may be equal or larger than the accepted angular deviation NA of the detector 106.

Figure 1B:
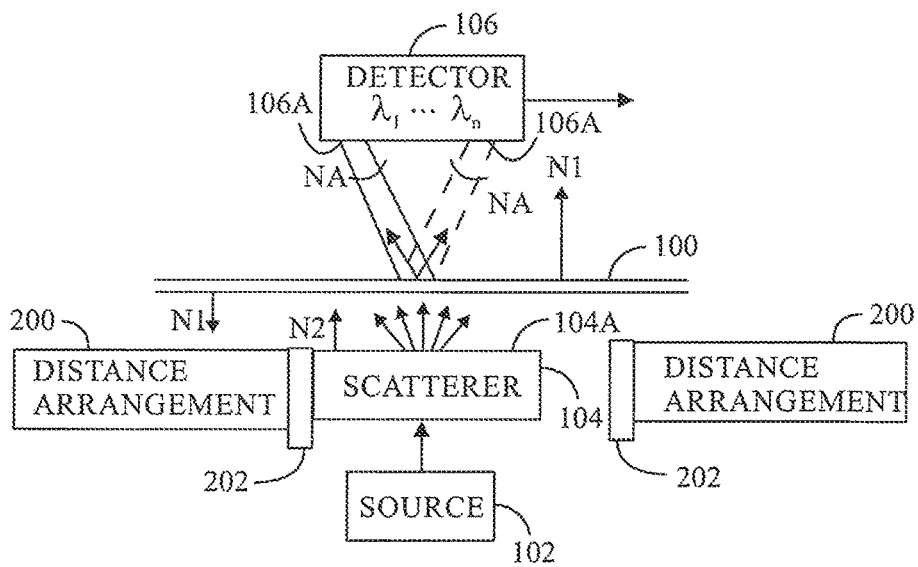
Figure 1C:
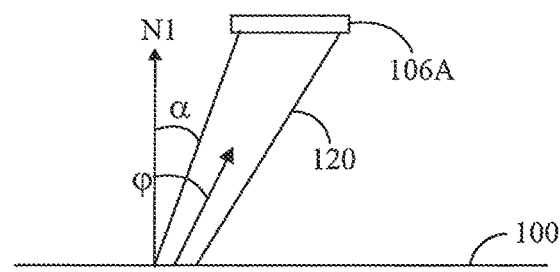

As can be seen in an example of FIG. 1C, all rays of the optical radiation 120 scattered from the paper web 100 toward the receiving aperture 106A of the detector 106 are in a direction which deviates from the normal N1 of the paper web 100.

Figure 1D:
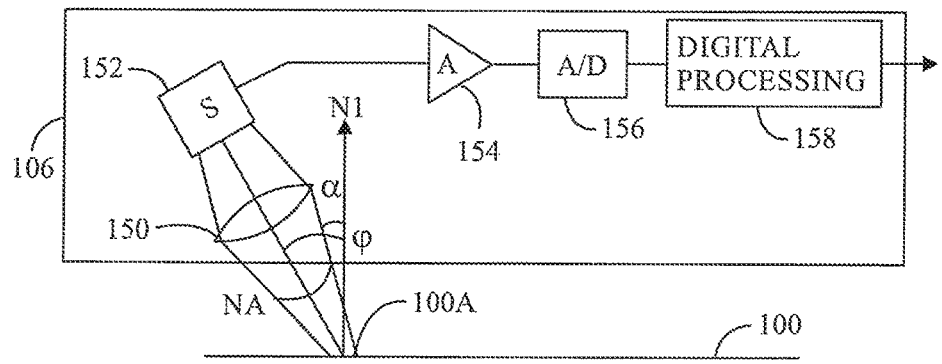

FIG. 1D illustrates an example for gathering the scattered optical radiation from the paper web 100. The target area 100A, from which the detector 106 gathers the optical radiation, is typically smaller than the illuminated area to which the scattering element 104 scatters the optical radiation. At least one optical component 150 such as one or more lenses or mirrors may be used to gather the optical radiation from the target are 100A. The numerical aperture (accepted angular deviation) NA of the at least one optical component 150 also defines an entrance aperture of the detector 106, and the entrance aperture corresponds to the aperture 106A shown in FIGS. 1A, 1B and 1C because it defines physical/angular limits within which the optical radiation may proceed from the paper web 100 to the detector 106. The at least one optical component 150 may image the target area 100A on the sensor 152 of the detector 106, although image forming is not necessary. The sensor 152 may then convert an intensity of the optical radiation to an electrical signal. The electrical signal may be amplified in an amplifier 154. The electrical signal, which is in an analog form, may then be converted into a digital form in an analog/digital converter 156. After this the electrical signal may proceed to a digital data processing part 158. Also in this Figure, the smallest angle α between the rays of the optical radiation 120 scattered from the paper web toward the sensor 152 of the detector 106 and the normal N1 of the paper web 100 is shown.

In an embodiment, the detector 106 may receive rays of the side-scattered optical radiation, directions of which deviate from the direction of the normal N1 of the paper web 100 by at least the smallest angle α, which may be the same as the angular deviation ND of the forward-scattered optical radiation 110. Thus, the smallest angle α is the same ND or larger up to 90°. The optical radiation source 102 may cause the angular deviation ND of the forward-scattered optical radiation. This is an alternative manner to define the angle between the side-scattered optical radiation received by the detector 106 and the direction of the normal N1 of the paper web 100. In an embodiment, the smallest angle α, which is the alternative interpretation of the predetermined angle, may be equal or larger than the accepted angular deviation NA of the detector 106.

In an embodiment, detector 106 may have at least one mirror in order to turn the optical radiation to a desired direction, which may allow to pack the detector 106 in compact case. In a corresponding manner, the apparatus may have at least one mirror between the source 102 and the scattering element 104 for allowing to pack them in compact case.

In an embodiment, the detector 106 may receive rays of the side-scattered optical radiation, directions of which deviate from the direction of the normal N1 of the paper web 100 by at least 5°, i.e. the smallest angle α is about 5°. Thus, the rays of the side-scattered optical radiation may be detected only if they are in the angular range about 5° to 90°. Because the angle 90° is parallel to the surface, the angular range may be about 5° to B, where B may at maximum be an angle between 80° and 90°, for example. B may at maximum be about 80°, 82°, 85°, 87° or 89°, for example.

In an embodiment, the apparatus may comprise a distance arrangement 200, and the distance arrangement 200 keeps the distance D between the transmitting surface 104A of the scattering element 104 and a surface of the paper web 100 constant. In this manner, an effect of a variation of the distance D can be decreased in or removed from the determination of the moisture value and the dry weight of the paper web 100.

In an embodiment, the distance arrangement 200 may set a first surface 108 of the paper web 100 and the scattering element 104 in a stabilized position with each other. The distance arrangement 200 may comprise at least one ejector 202, which causes a controlled air pressure effect with respect to the environment of the at least one ejector 202 to the paper web 100. The air pressure effect may be suction, for example. As a result, the apparatus may perform the measurements in a semi-contacting manner. The moving paper web 100 may also be in an actual physical contact with the scattering element 104, or there may be a non-zero distance D between the scattering element 104 and the paper web 100. The distance D, which as stated may be zero or non-zero, may be a controlled. A surface of the scattering element 104 may be a plate-like structure which is on one side of the paper web 100 and by which the paper web 100 may be supported during the movement in a machine direction of production.

In an embodiment, the transmitting surface 104A of the scattering element 104 and the paper web 100 may touch each other.

In an embodiment an example of which is illustrated in FIG. 1A, the apparatus may comprise a distance measuring unit 204. The measuring unit 204 may measure the distance D between the transmitting surface 104A of the scattering element 104 and a surface of the paper web 100. The distance measurement, which may be the prior art, per se, may be optical, magnetic or be based on radio active radiation, for example. The detector 106 may compensate an effect of a variation of the distance D in the determination of the moisture value and the dry weight of the paper web 100.

In an embodiment, the distance measuring unit 204 may measure a tilt between between the transmitting surface 104A of the scattering element 104 and the surface of the paper web 100. The detector 106 may compensate an effect of the tilt in the determination of the moisture value and the dry weight of the paper web 100. The tilt may affect the optical power distribution received by the paper web 100. The tilt may also cause a potential change in a distribution of the optical power of the optical radiation scattered from the paper web 100. Hence, a variation of the tilt may cause a variation in the optical power received by the detector 106. However, the effect of the tilt may be determined by calibration measurements using at least one tilt value. When the effect is determined, it can be eliminated or reduced in the measurements of moisture and dry weight of the paper web 100. The effect of the varying tilt may be determined at any moment or it may be statistically approximated in a time-window.

Figure 2:
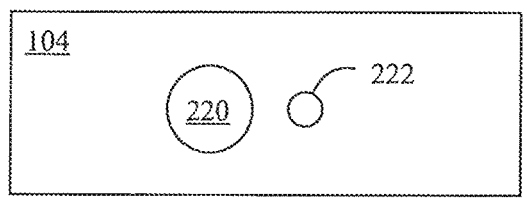
FIG. 2 illustrates an example of the scattering element.

FIG. 2 illustrates an example of the scattering element 104. The scattering element 104 may have an optical aperture 220 for outputting the scattered optical radiation toward the paper web 100. The optical aperture 220 has the scattering surface 104A. The scattering element 104 may also have a first opening 222 for outputting air or gas. The first opening 222 may be a valve. A flow of air or gas may be used to clean optical surfaces of the detector 106 (see also FIG. 3). Pressurized air or gas can be fed through a pipe to the first opening 222. The first opening 222 may be a mouth of the pipe, for example. In an embodiment, a sudden blast of air or gas may be output through the opening or valve 222.

Figure 3:
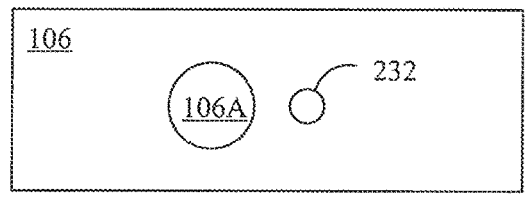
FIG. 3 illustrates an example of a detector.

FIG. 3 illustrates an example of the detector 106. The detector 106 has the optical aperture 106A for receiving the scattered optical radiation from the paper web 100. The detector 106 may also have a second opening 232 for outputting air or gas. The second opening 232 may be a valve. A flow of air or gas may be used to clean optical surfaces of the scattering element 104 (see also FIG. 2). Pressurized air or gas can be fed through a pipe to the second opening 232. The second opening 232 may be a mouth of the pipe, for example. In an embodiment, a sudden blast of air or gas may be output through the opening or valve 222.

By cleaning the optical surfaces of at least one of the scattering element 104 and the detector 106 with air or gas increases reliability of the optical measurements.

Figure 4:
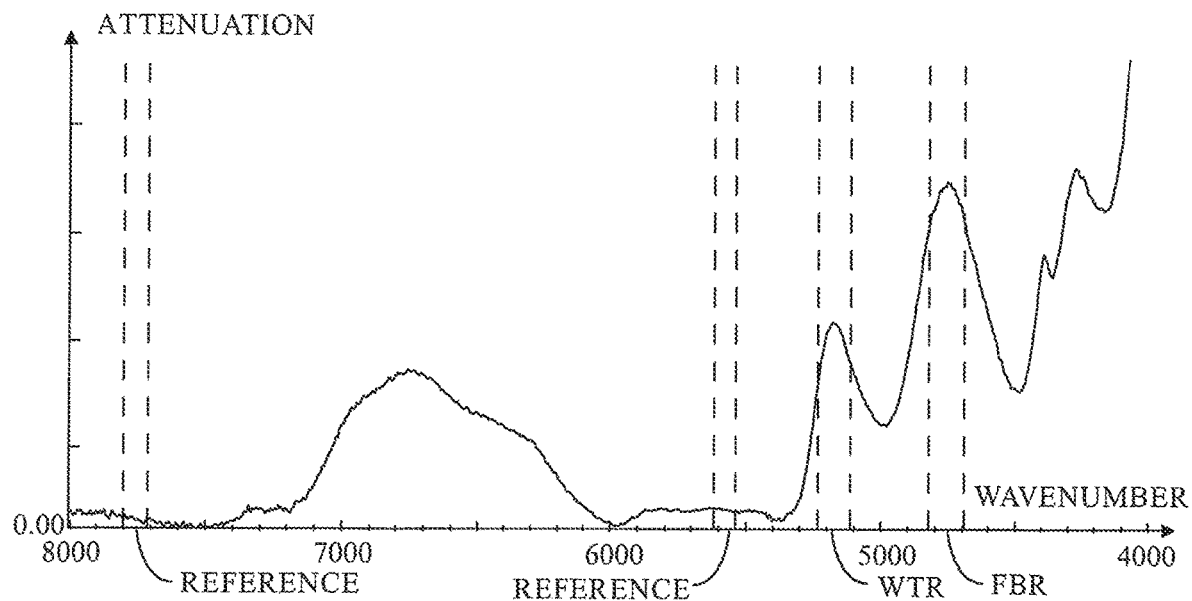
FIG. 4 illustrates an example of an attenuation spectrum and examples of optical bands which the paper web measurement apparatus may utilize.

Although a person skilled in the art knows how to measure the moisture value, the moisture percentage, the water weight and the dry weight of the paper web 100 optically, per se, here is some background for the measurement, with reference to FIG. 4. The horizontal axis is a wavenumber and the vertical axis is optical attenuation in an arbitrary scale. When the optical radiation, which may be in a range of infrared spectrum of light, for example, passes through the paper web 100, it is sensitive at certain wavelengths to cellulose and potential other dry material, and water. The sensitivity can be characterized as strong attenuation at certain wavelength bands. In the detector 106, the optical radiation scattered by the paper web 100 is collected by detection optics, which defines or has as a part the aperture 106A. The optical radiation may also be filtered such that only the bands, which are measured, are allowed to actual sensing semiconductor component(s). Then the optical radiation is detected by the sensing semiconductor component(s), such as InGaAs quad-sensors (Indium Gallium Arsenide) of the detector 106, without limiting to the InGaAs-sensor(s). The sensing component(s) may be temperature controlled.

The detector 106 may utilize at least one absorption wavelength band of cellulose material, at least one absorption wavelength band of water, and at least one wavelength band for determining a reference parameter. The optical band for dry weight determination may include 2110 nm wavelength (corresponds to wavenumber 4740, see FBR in FIG. 4), for example, where the fiber material such as cellulose has a strong specific absorption. An optical band for measuring water content may include 1450 nm (corresponds to wavenumber 6900, not marked in FIG. 4) and/or 1940 nm (corresponds to wavenumber 5155, see WTR in FIG. 4), for example, where water has a strong specific absorption. The detector 106 may measure at least one reference (see REFERENCE in FIG. 4), which has no or only weak sensitivity to dry matter and water in order to determine the height/strength of the absorption of the dry matter and water. The detector 106 may measure the references, wavenumbers of which may be at about 7800 and 5560, for example, for a base line. The base line, in turn, may be used to determine a potential tilting of measured attenuation/absorption levels as a function of a wavelength/wavenumber. Instead of an infrared region, other optical regions may be utilized in the measurements. The bandwidth of a measured band may vary from about a nanometer to a few nanometers, for example.

The dry matter measurement is an absolute measurement in a sense that a detected attenuation is calibrated to match with a real dry matter content, when the measuring apparatus is manufactured and potentially also later during a recalibration. The moisture percentage is typically a relative measurement where a measured water/moisture content is compared with a measured dry matter content.

An increasing ash content of the dry matter of the paper web 100 also increases scattering of the optical radiation passing through the paper web 100, which, in turn, can be seen in increasing attenuation. Correspondingly, with a decreasing ash content, also the attenuation decreases. In this way, the ash content can be detected and taken into account in the dry matter measurement.

Figure 5:
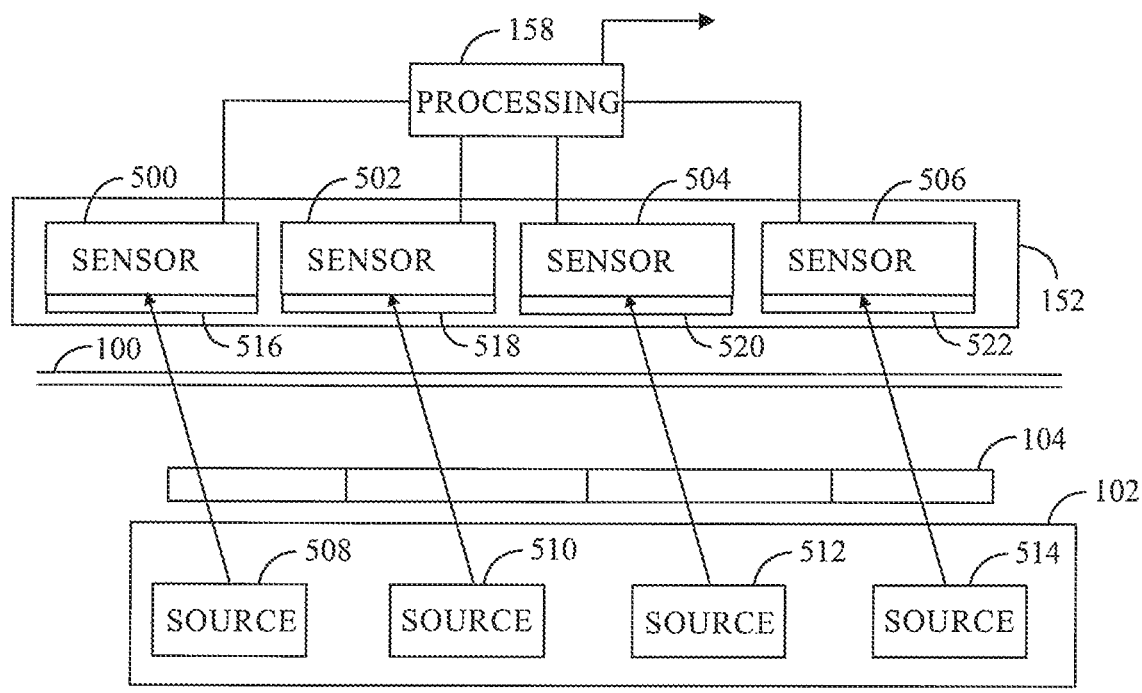
FIG. 5 illustrates an example where the detector may comprise a plurality of semiconductor sensor units.

FIG. 5 illustrates an example where the detector 106 may comprise a plurality of semiconductor sensor units 500, 502, 504, 506 such as the InGaAs-sensors. The detector 106 may also comprise a data processing unit 158 which processes the electrical signals from the sensor units 500 to 506. Each of the sensor units 500 to 506 may have a corresponding optical radiation sub-source 508, 510, 512, 514. That is, a sensor unit 500 to 506 and a sub-source 508 to 514 form a pair such that from one sub-source 508 to 514 the optical radiation propagates to only one sensor unit 500 to 506. In an embodiment, each sensor unit 500 to 506 may detect only one wavelength band, for example. In an embodiment, at least two sensor units 500 to 506 may detect different wavelength bands, for example. In an embodiment, any two sensor units 500 to 506 may detect different wavelength bands, i.e. all sensor units 500 to 506 may detect different wavelength bands, for example. One sensor unit may comprise one or more sensor sub-units.

In an embodiment shown in FIG. 5, the scattering element 104 may comprise a plurality of scattering sub-elements (see vertical lines dividing the scattering element 104 in parts). In an embodiment, at least two pairs of sub-sources 508 to 514 and sensor units 500 to 506 may have a scattering sub-element of their own such that the optical radiation propagating therebetween passes only through said scattering sub-element. The scattering sub-elements may be tuned to the wavelengths they scatter for the measurement. The material and/or the particle sizes may be optimized in order to have an optimum scattering. The optimization may be based on a theory, one or more simulations or one or more tests.

In an embodiment, there may be filters 516 to 522 in front of the sensor units 500 to 506 in order to detect desired wavelengths with the sensor units 500 to 506. In an embodiment, at least two filters 516 to 522 pass different wavelength bands to the sensor units 500 to 506. In an embodiment, any two filters 516 to 522 pass different wavelength bands to the sensor units 500 to 506.

Figure 6:
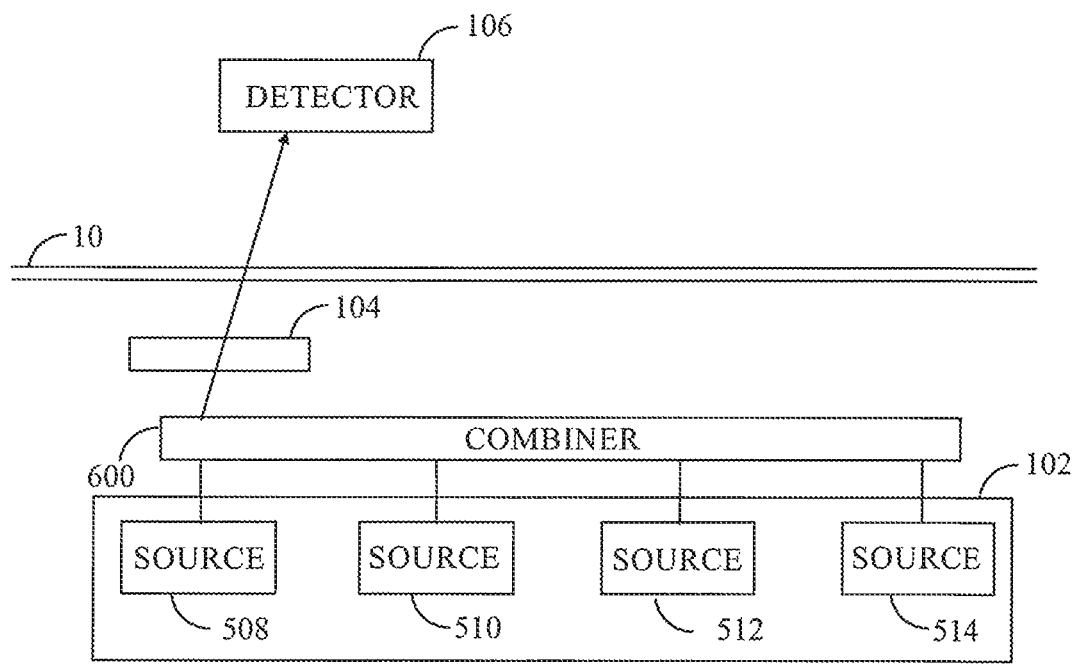
FIG. 6 illustrates an example a combiner that may combine optical radiation from a plurality of optical sub-sources.

FIG. 6 illustrates an example where a combiner 600 may combine optical radiation from a plurality of optical sub-sources 508 to 514 and direct the combined optical radiation to the scattering element 104.

In an embodiment associated to FIGS. 5 and 6, at least two sub-sources 508 to 514 may output different wavelength bands. In an embodiment, any two sub-sources 508 to 514 may output different wavelength bands. In this example, filters 516 to 522 in front of the sensor units 500 to 506 may not be necessary (see FIG. 5). The optical sub-sources 508 to 514 may comprise leds, for example.

Figure 7:
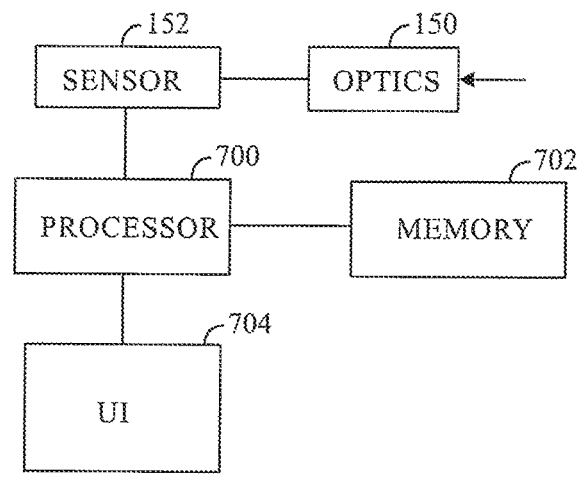
FIG. 7 illustrates an example of the detector with data processing.

FIG. 7 illustrates an example of the detector 106, which comprise the at least one optical component 150, the sensor 152, at least one processor 700 and at least one memory 702 which may include a suitable computer program. The detector 106 may comprise or may be connected directly or indirectly with a user interface 704, which may include a keyboard, a screen and/or a touch screen, for example. The user interface 704 may be used present the measurement results to a user. Additionally, the user may input data and/or commands through the user interface 704 to the measurement apparatus.

Figure 8:
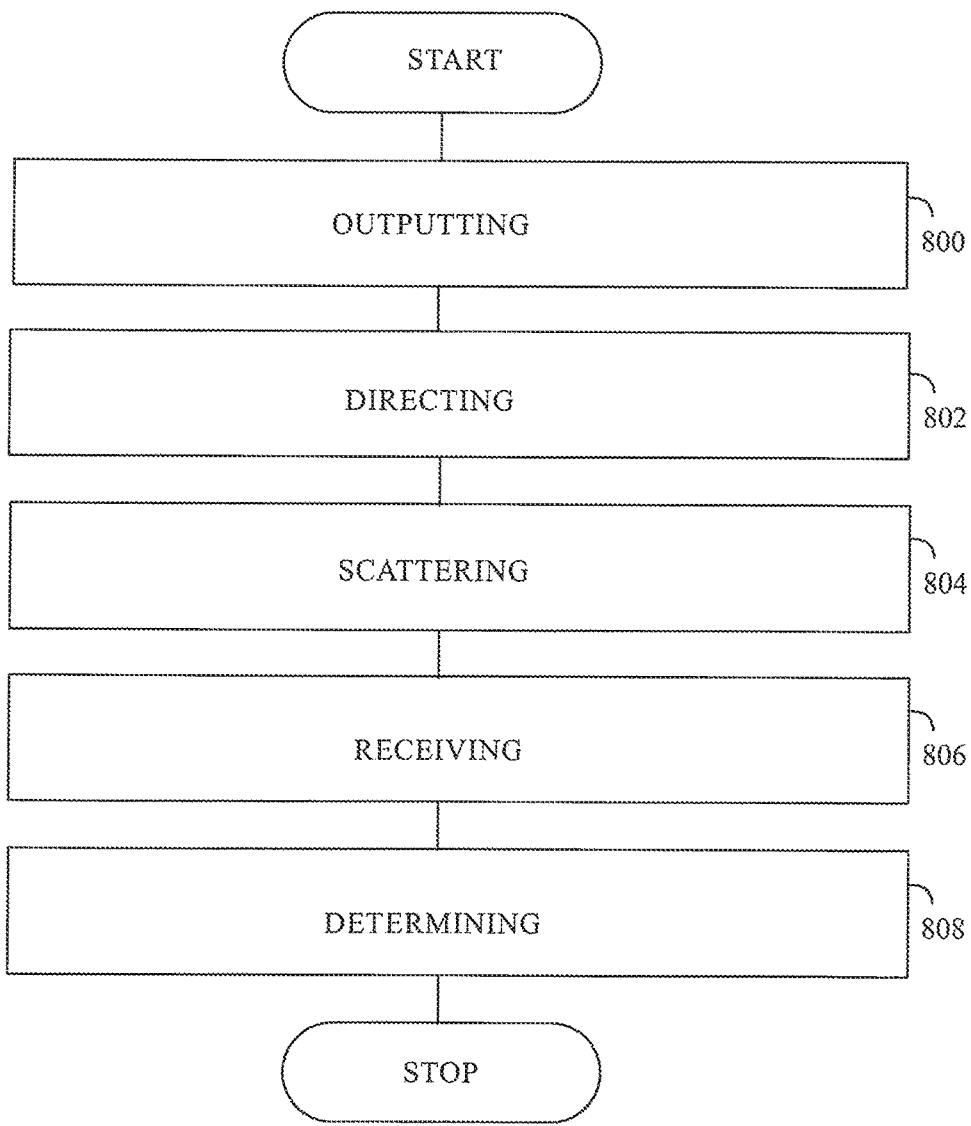
FIG. 8 illustrates of an example of a flow chart of a measuring method.

FIG. 8 is a flow chart of the measurement method. In step 800, an optical radiation source 102 outputs optical radiation toward a scattering element 104. In step 802, the scattering element 104 scatters the optical radiation. In step 804, a transmitting surface 104A of the scattering element 104 directs the optical radiation, in a scattered manner, toward the moving paper web 100, where a normal N2 of said transmitting surface 104A of the scattering element 104 is parallel to a normal N1 of the paper web 100, and said transmitting surface 104A and a detector 106 of the apparatus are on opposite sides of the paper web 100. In step 806, at least a part of the optical radiation, which is side-scattered from the moving paper web 100, is received by the detector 106, while the optical radiation 110, which is forward-scattered from the moving paper web 100 is rejected by the detector 106. In step 808, a moisture value and a dry weight of the paper web 100 are determined by the detector 106 on the basis of spectral information on the received optical radiation.

The method of data processing in the detector 106 may be implemented as a logic circuit solution or computer program. The computer program may be placed on a computer program distribution means for the distribution thereof. The computer program distribution means is readable by a data processing device, and it encodes the computer program commands for the data processing, may carry out the measurements.

It will be obvious to a person skilled in the art that, as technology advances, the inventive concept can be implemented in various ways. The invention and its embodiments are not limited to the example embodiments described above but may vary within the scope of the claims.

The invention claimed is:

1. A measurement apparatus of a moving paper web, wherein:
the apparatus comprises an optical radiation source that is configured to output optical radiation toward a scattering element of the measurement apparatus;
the scattering element is configured to scatter the optical radiation, and a transmitting surface of the scattering element is configured to direct the optical radiation in a scattered manner toward the moving paper web;
a distance between said transmitting surface of the scattering element and a surface of the paper web is known, and the transmitting surface and a detector of the apparatus are on opposite sides of the paper web;
the detector is configured to receive at least a part of the optical radiation, which is side-scattered from the moving paper web, the side-scattered optical radiation deviating by a predetermined angle from a direction that extends from the scattering element to the paper web, and reject the optical radiation that has passed directly through the moving paper web without scattering;
the detector is configured determine a moisture value and a dry weight of the paper web on a basis of spectral information on the received optical radiation and the known distance.

2. The measurement apparatus of claim 1, wherein the detector is configured to receive the side-scattered optical radiation only from directions, which deviate from the direction of the normal of the paper web by at least a predetermined amount.

3. The measurement apparatus of claim 1, wherein the detector is configured to receive rays of the side-scattered optical radiation, where a direction of a middle ray deviates from the direction perpendicular to the paper web by at least an angle that corresponds to an angular deviation of forward-scattered optical radiation.

4. The measurement apparatus of claim 1, wherein the detector is configured to receive rays of the side-scattered optical radiation, where a direction of a middle ray deviates from the direction perpendicular the paper web by at least 8°.

5. The measurement apparatus of claim 1, wherein apparatus comprises a distance arrangement, and the distance arrangement is configured to keep the distance between the transmitting surface of the scattering element and the surface of the paper web constant.

6. The measurement apparatus of claim 1, wherein the transmitting surface of the scattering element and the paper web are configured to touch each other.

7. The measurement apparatus of claim 1, wherein the apparatus comprises a distance measuring unit, and the distance measuring unit is configured to measure the distance between the transmitting surface of the scattering element and the surface of the paper web, and the detector is configured to compensate an effect of a variation of the distance in the determination of the moisture value and the dry weight of the paper web.

8. The measurement apparatus of claim 7, wherein the distance measuring unit is configured to measure a tilt between the transmitting surface of the scattering element and the surface of the paper web, and the detector is configured to compensate an effect of the tilt in the determination of the moisture value and the dry weight of the paper web.

9. The measurement apparatus of claim 1, wherein the scattering element comprises a first opening for outputting air or gas toward the detector.

10. The measurement apparatus of claim 1, wherein the detector comprises a second opening for outputting air or gas toward the scattering element.

11. The measurement apparatus of claim 1, wherein normal of said transmitting surface of the scattering element is parallel to a normal of the paper web.

12. The measurement apparatus of claim 1, wherein detector comprises a one or more processors; and
one or more memories including computer program code;
the one or more memories and the computer program code configured to, with the one or more processors, cause apparatus at least to perform the determination of the moisture value and the dry weight of the paper web on the basis of spectral information on the received optical radiation.

13. A method of measuring a moving paper web, comprising:
outputting, by an optical radiation source, optical radiation toward a scattering element;
scattering the optical radiation by the scattering element;

directing the optical radiation, by a transmitting surface of the scattering element, in a scattered manner toward the moving paper web, where a distance between said transmitting surface of the scattering element and a surface of the paper web is known, and the transmitting surface and a detector of a measurement apparatus are on opposite sides of the paper web;

receiving, by the detector, at least a part of the optical radiation, which is side-scattered from the moving paper web and rejecting the optical radiation that has passed directly through the moving paper web without scattering, the side-scattered optical radiation deviating by a predetermined angle that extends from a direction from the scattering element to the paper web; and determining, by the detector, a moisture value and a dry weight of the paper web on the basis of spectral information on the received optical radiation and the known distance.

14. The measurement apparatus according to claim 1, wherein the detector and the optical radiation source are provided on opposite surfaces of the paper web.

\* \* \* \* \*